United States Patent
Chan et al.

(10) Patent No.: US 7,939,283 B2
(45) Date of Patent: May 10, 2011

(54) ANALYTE BINDING TURBIDITY ASSAY

(75) Inventors: Teresa Chan, Wayland, MA (US);
Joseph F. Lawlor, Arlington, MA (US);
Gordon C. Siek, Somerville, MA (US);
Arleen Chase, Billerica, MA (US);
Joseph D. Musto, Dover, MA (US)

(73) Assignee: Fisher Scientific Company L.L.C., Pittsburgh, PA (US)

( * ) Notice: Subject to any disclaimer, the term of this patent is extended or adjusted under 35 U.S.C. 154(b) by 1441 days.

(21) Appl. No.: 10/194,638

(22) Filed: Jul. 12, 2002

(65) Prior Publication Data
US 2003/0082589 A1 May 1, 2003

Related U.S. Application Data

(60) Provisional application No. 60/334,748, filed on Nov. 1, 2001.

(51) Int. Cl.
*G01N 33/53* (2006.01)
*G01N 33/543* (2006.01)

(52) U.S. Cl. ........ 435/7.5; 435/7.1; 435/7.94; 435/7.92; 435/4; 436/518; 436/523; 436/525; 436/528

(58) Field of Classification Search .................. 435/969, 435/7.5, 7.1, 7.94, 7.92, 4; 436/518, 523, 436/525, 528, 535, 808
See application file for complete search history.

(56) References Cited

U.S. PATENT DOCUMENTS

| | | | |
|---|---|---|---|
| 4,184,849 A | 1/1980 | Cambiaso et al. | |
| 4,185,084 A | 1/1980 | Mochida et al. | |
| 4,659,678 A | 4/1987 | Forrest et al. | |
| 5,362,655 A | 11/1994 | Schenk et al. | |
| 5,384,265 A * | 1/1995 | Kidwell et al. | 436/525 |
| 5,401,636 A | 3/1995 | Craig | |
| 5,434,088 A * | 7/1995 | Ikeda et al. | 436/525 |
| 5,437,981 A | 8/1995 | Deger et al. | |
| 5,583,054 A | 12/1996 | Ito et al. | |
| 5,589,401 A * | 12/1996 | Hansen et al. | 436/525 |
| 5,643,731 A * | 7/1997 | Bosslet et al. | 435/7.1 |
| 5,693,214 A | 12/1997 | Abe et al. | |
| 5,693,784 A | 12/1997 | Ekenberg | |
| 5,695,901 A | 12/1997 | Selim | |
| 5,736,349 A | 4/1998 | Sasaki et al. | |
| 5,792,606 A | 8/1998 | Deger et al. | |
| 6,087,188 A | 7/2000 | Johansen et al. | |
| 6,096,563 A | 8/2000 | Hajizadeh et al. | |
| 6,274,325 B1 | 8/2001 | Deger et al. | |
| 6,753,190 B1 * | 6/2004 | Okada et al. | 436/518 |

FOREIGN PATENT DOCUMENTS

| | | |
|---|---|---|
| EP | 0 302 715 | 2/1989 |
| EP | 0 557 546 | 9/1993 |
| WO | WO 00/73797 | 12/2000 |

OTHER PUBLICATIONS

Notification of Transmittal of The International Search Report or the Declaration of May 2, 2003 for International Application No. PCT/US02/33891.
Gosling, James P., "A Decad of Development in Immunoassay Methodology" *Clin. Chem.* 36/8, 1408-1427 (1990).
Linvnah et al., "Three-dimensional structures of avidin and avidin-biotin complex", *Proc. Natl. Acad. Sci.* USA vol. 90, pp. 5076-5080m Hybe 1993 Biochemistry.
Wilchek et al., "Understanding and Application of Biorecognition" *Biological Chemistry* Jul. 26, 2001 1-3.
*Chemical and Engineering News* Reaching Out—Extended polymers have dramatic effect on molecular recognition p. 13, Jul. 23, 2001.
*Chemical and Engineering News* These Antibodies Go All the Way—Researchers develop antibody-life-ligand complexes that are fit to be tied and never dissociate p. 36-37, Jul. 23, 2001.

* cited by examiner

*Primary Examiner* — Jacob Cheu
*Assistant Examiner* — Pensee T Do
(74) *Attorney, Agent, or Firm* — Fish & Richardson P.C.

(57) ABSTRACT

Assays, such as immunoassays, and related articles are disclosed.

8 Claims, 9 Drawing Sheets

ANALYTE BINDING TURBIDITY ASSAY

CROSS-REFERENCE TO RELATED APPLICATION

This application claims priority under 35 U.S.C. §119 to U.S. Provisional Patent Application Ser. No. 60/334,748, filed on Nov. 1, 2001, and entitled "Assay," the entire contents of which are hereby incorporated by reference.

TECHNICAL FIELD

The invention relates to assays, such as immunoassays, and related articles.

BACKGROUND

Immunoassays can be used to measure the concentration of antigens in a solution, such as serum. Often, such assays involve one or more steps in which a mixture is washed so that certain chemical species are removed from the mixture prior to measuring a predetermined parameter (e.g., turbidity, absorbance, fluorescence or radioactivity).

SUMMARY

In general, the invention relates to assays, such as immunoassays, and related articles. Typically, the assays involve forming a network of particles that are interconnected by binding partners (an agglomeration). It is believed that, in some embodiments, the formation of one or more agglomerations can increase the speed with which the assay detects one or more analytes of interest and/or increase the sensitivity of the assay toward one or more analytes.

In one aspect, the invention features an article for binding an analyte (e.g., an antigen). The article includes a particle, and first and second ligands (e.g., an antibody and avidin, respectively). The first ligand is capable of binding to the analyte, and the second ligand is bound to either the particle or the first ligand. The second ligand has at least two binding sites for a third ligand (e.g., biotin) that is a binding partner with the second ligand.

Typically, the first ligand (e.g., an antibody) is bound to the particle directly or via the second ligand (e.g., avidin).

In some embodiments, the second ligand is not bound to both the first particle and the first ligand.

The article can further include the third ligand bound to the second ligand. The third ligand can have only one binding site for the second ligand.

The second and third ligands can have an affinity constant of at least about $1 \times 10^4$ liters per mole.

The second and third ligands can have an affinity constant that is greater than an affinity constant of the first ligand and the analyte.

The article can further include an additional particle bound to the third ligand. The article can further include a fourth ligand bound to the additional particle. The fourth ligand can be capable of binding to the analyte. The article can further include an analyte bound to the first and/or fourth ligands.

The article can further include a fourth ligand bound to a second particle (e.g., without having a third ligand bound to the second particle). The analyte can be bound to the first and/or fourth ligand.

The analyte can be, for example, an antibody, a vitamin, a pesticide, an antigen, a protein antigen, a drug, a steroid, a peptide, an oligonucleotide, an oligosaccharide, a hormone or a toxin.

The particle(s) can be, for example, selected from a metal particle, a latex particle, a silica particle, a glass particle, a paramagnetic particle, a polymer particle, an erythrocyte particle or a liposome particle. As examples, the particle(s) can be selected from a colloidal gold particle or a polymeric particle.

The first ligand can be, for example, selected from antibodies, antigens, lectins, receptors, binding proteins, co-factors, vitamins, peptides, oligonucleotides, metal chelating agents, polysaccharides or derivatives thereof.

The second ligand can be, for example, selected from a biotin-binding protein, an immunoglobulin, lectin, or a metal chelating agent. For example, the second ligand can be a biotin binding protein, such as avidin.

The third ligand can be, for example, selected from biotin, metal ions, protein A, protein G, haptens and saccharides. For example, the third ligand can be biotin.

The fourth ligand can be, for example, selected from antibodies, antigens, lectins, receptors, binding proteins, co-factors, vitamins, peptides, oligonucleotides, metal chelating agents, polysaccharides or derivatives thereof.

The article can further include a plurality of the first ligands bound to the first particle.

The article can further include a plurality of the second ligands with at least some of the plurality of the first ligands having one of the plurality of the second ligands bound thereto.

The article can further include a plurality of the second ligands and a plurality of the first particles with at least some of the plurality of the first particles having one of the plurality of the second ligands bound thereto, the plurality of particles forming an agglomeration.

In another aspect, the invention features an agglomeration that includes a plurality of particles, a plurality of first ligands (e.g., a plurality of one or more antibodies), a plurality of second ligands (e.g., a plurality of avidin molecules) and a plurality of third ligands (e.g., a plurality of biotin molecules). The first ligands are capable of binding to an analyte (e.g., an antigen), and each of the plurality of first ligands is bound to a particle. Each of the plurality of second ligands is bound to one of the plurality of particles or one of the plurality of first ligands. Each of the plurality of third ligands is bound to one of the plurality of second ligands. Each of the plurality of second ligands has at least two binding sites for the third ligand, and each of the plurality of third ligands has only one binding site for the second ligand.

In some embodiments, each of the second ligands is not bound to both one of the plurality of particles and one of the plurality of first ligands.

In certain embodiments, the second and third ligands have an affinity constant of at least about $1 \times 10^4$ liters per mole.

In some embodiments, an affinity constant of the second and third ligands is greater than an affinity constant of the first ligand and the analyte.

In certain embodiments, at least some of the plurality of particles are selected from, for example, metal particles, latex particles, silica particles, glass particles, paramagnetic particles, polymer particles, erythrocyte particles and liposome particles.

At least some of the plurality of first ligands can be, for example, selected from antibodies, antigens, lectins, receptors, binding proteins, co-factors, vitamins, peptides, oligonucleotides, metal chelating agents, polysaccharides or derivatives thereof.

At least some of the plurality of second ligands can be, for example, selected from the group consisting of a biotin-binding protein, an immunoglobulin, lectin, or a metal chelating agent.

At least some of the plurality of third ligands can be, for example, selected from the group consisting of biotin, metal ions, protein A, protein G, haptens or saccharides.

The agglomeration can further include a plurality of analytes with each analyte being bound to two of the plurality of first ligands.

The analyte can be, for example, selected from the group consisting of antibodies, vitamins, pesticides, antigens, protein antigens, drugs, steroids, peptides, oligonucleotides, oligosaccharides, hormones or toxins.

At least some of the plurality of particles can have more than one of the plurality of first ligands bound thereto.

The agglomeration can further include a plurality of fourth ligands bound to a plurality of second particles with an analyte bound to both the first ligand and the fourth ligand.

In a further aspect, the invention features an article for binding an analyte (e.g., an antigen) that includes a first ligand (e.g., an antibody) capable of binding to the analyte, a second ligand (e.g., avidin) bound to the first ligand, and a third ligand bound (e.g., biotin) to the second ligand. The second ligand has at least two binding sites for the third ligand, and the third ligand has only one binding site for the second ligand.

In some embodiments, the second and third ligands have an affinity constant of at least about $1 \times 10^4$ liters per mole.

In certain embodiments, the second and third ligands have an affinity constant that is greater than an affinity constant of the first ligand and the analyte.

The article can further include a particle bound to the third ligand.

The article can further include a fourth ligand bound to the particle with the fourth ligand being capable of binding to the analyte.

The article can further include an analyte bound to the first and fourth ligands.

The analyte can be, for example, selected from antibodies, vitamins, pesticides, antigens, protein antigens, drugs, steroids, peptides, oligonucleotides, oligosaccharides, hormones or toxins.

The first ligand can be, for example, selected from antibodies, antigens, lectins, receptors, binding proteins, co-factors, vitamins, peptides, oligonucleotides, metal chelating agents, polysaccharides or derivatives thereof.

The second ligand can be, for example, a biotin-binding protein, an immunoglobulin, lectin, or a metal chelating agent.

The third ligand can be selected from the group consisting of biotin, metal ions, protein A, protein G, haptens or saccharides. The third ligand can be, for example, biotin.

The particle can be, for example, selected from metal particles, latex particles, silica particles, glass particles, paramagnetic particles, polymer particles, erythrocyte particles or liposome particles. As an example, the particle can be a polymeric particle or a colloidal gold particle.

The fourth ligand can be, for example, selected from antibodies, antigens, lectins, receptors, binding proteins, co-factors, vitamins, peptides, oligonucleotides, metal chelating agents, polysaccharides or derivatives thereof.

The article can further include a plurality of the first ligands bound to the first particle.

The article can further include a plurality of the second ligands with at least some of the plurality of the first ligands having one of the plurality of the second ligands bound thereto.

In one aspect, the invention features an agglomeration that includes a plurality of particles, a plurality of first ligands (e.g., a plurality of antibodies) capable of binding to an analyte (e.g., an antigen), a plurality of second ligands (e.g., a plurality of avidin molecules) with each of the plurality of second ligands being bound to a first ligand, and a plurality of third ligands (e.g., a plurality of biotin molecules). Each of the plurality of third ligands being bound to one of the plurality of second ligands, each of the plurality of third ligands being bound to a particle. Each of the plurality of second ligands has at least two binding sites for the third ligand, and each of the plurality of third ligands has only binding site for the second ligand.

In some embodiments, the second and third ligands have an affinity constant of at least about $1 \times 10^4$ liters per mole.

In certain embodiments, an affinity constant of the second and third ligands is greater than an affinity constant of the first ligand and the analyte.

At least some of the plurality of particles can be, for example, selected from metal particles, latex particles, silica particles, glass particles, paramagnetic particles, polymer particles, erythrocyte particles or liposome particles.

At least some of the plurality of first ligands can be, for example, selected from antibodies, antigens, lectins, receptors, binding proteins, co-factors, vitamins, peptides, oligonucleotides, metal chelating agents, polysaccharides or derivatives thereof.

At least some of the plurality of second ligands can be, for example, selected from a biotin-binding protein, an immunoglobulin, lectin, or a metal chelating agent.

At least some of the plurality of third ligands can be, for example, selected from biotin, metal ions, protein A, protein G, haptens or saccharides.

The agglomeration can further include a plurality of analytes with each analyte being bound to two of the plurality of first ligands.

The analyte can be, for example, selected from antibodies, vitamins, pesticides, antigens, protein antigens, drugs, steroids, peptides, oligonucleotides hormones or toxins.

At least some of the plurality of particles can have more than one of the plurality of first ligands bound thereto.

In another aspect, the invention features a method of performing an assay for an analyte (e.g., an antigen) that includes linking first and second particles via a non-covalent bond between first and second ligands (e.g., biotin and avidin, respectively). The first ligand has only one binding site for the second ligand, and the second ligand has at least two binding sites for the first ligand. The first ligand is bound to the first particle, and the second ligand is bound to either the second particle or a third ligand (e.g., an antibody). The second ligand is not bound to both the second particle and the third ligand, the third ligand is bound to the second particle, and the third ligand is capable of binding to the analyte.

The method can further include binding the third ligand to the analyte.

The second particle can have a fourth ligand bound thereto with the fourth ligand being capable of binding to the analyte.

The method can further include binding the analyte to the third and fourth ligands.

The method can further include binding the analyte to both the third ligand and to a fourth ligand attached to a third particle.

In some embodiments, the method forms an agglomeration.

In another aspect, the invention features a method of performing an assay for an analyte (e.g., an antigen) that includes linking a particle and a first ligand (e.g., an antibody) via a non-covalent bond between a second ligand (e.g., biotin) and a third ligand (e.g., avidin). The second ligand has only one binding site for the third ligand, and the third ligand has at least two binding sites for the second ligand. The second ligand is bound to the particle, the third ligand is bound to the first ligand, and the first ligand is capable of binding to the analyte.

The method can further include binding the first ligand to the analyte.

The first ligand can be bound to a second particle.

The first particle can have a fourth ligand bound thereto with the fourth ligand being capable of binding to the analyte.

The method can further include binding the analyte to the first and fourth ligands.

In some embodiments, the method can form an agglomeration.

DETAILED DESCRIPTION

Figure 1:
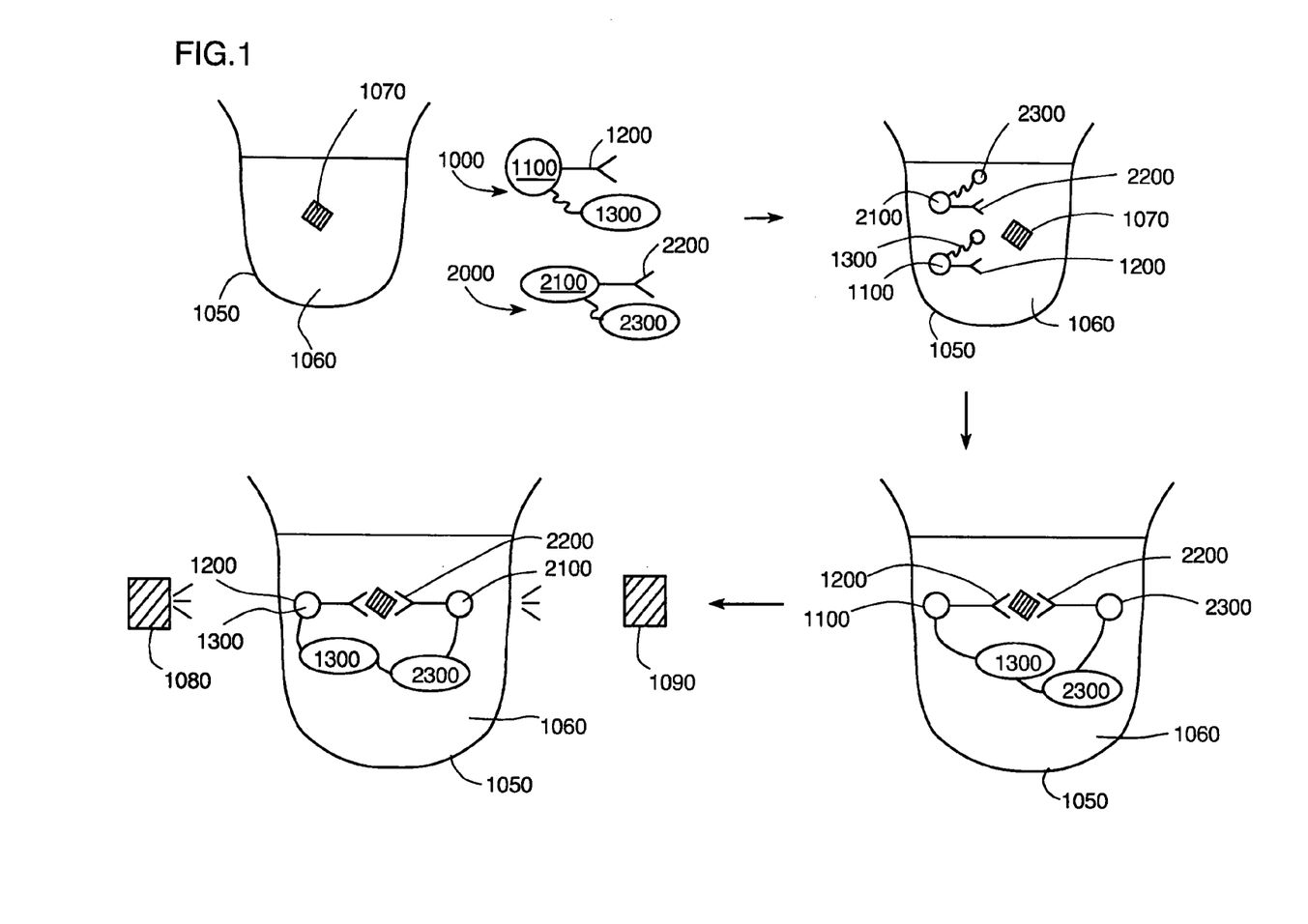
FIG. 1 is a schematic representation of an embodiment of a method.

FIG. 1 shows a schematic representation of a method of performing an assay.

A first article 1000 and a second article 2000 are introduced into a container 1050 containing a sample (e.g., a body fluid) 1060 with an analyte (e.g., an antigen, such as a protein antigen) 1070. Article 1000 includes a particle 1100 having bonded thereto an antibody 1200 and an avidin molecule 1300 (e.g., Streptavidin, available from Sigma Chemical Co. St. Louis, Mo. Article 2000 includes a particle 2100 having bonded thereto an antibody 2200 and a biotin molecule 2300. Articles 1100 and 2100 are linked via an interaction (e.g., a non-covalent bond) between avidin molecule 1300 and biotin molecule 2300, and antibodies 1200 and 2200 bond to analyte 1070 to form an analyte-antibody complex. Formation of the analyte-antibody complex can occur before, after or simultaneously with formation of the avidin-biotin interaction. The presence of the analyte-antibody complex is then determined using techniques such as, for example, light scattering and/or light absorbance using a light source 1080 and a detector 1090. Other techniques involving, for example, fluorescence can be used.

Figure 2:
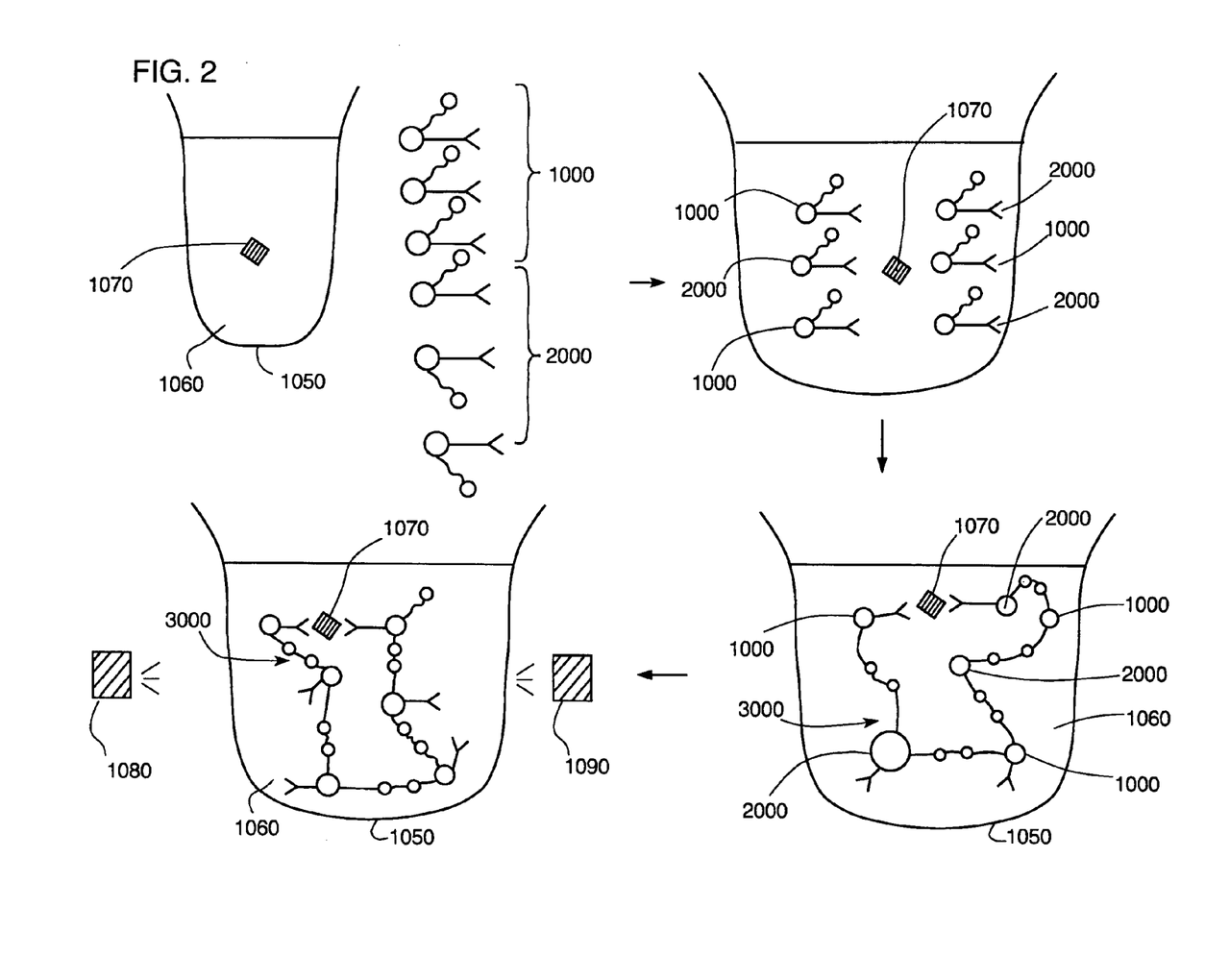
FIG. 2 is a schematic representation of an embodiment of a method.

FIG. 2 shows a schematic representation of a method of performing an assay.

In a first step, a plurality of first articles 1000 and a plurality of second articles 2000 are introduced into container 1050 containing sample 1060 with analyte 1070. Articles 1000 and 2000 form an agglomeration 3000 via a combination of avidin-biotin interactions (e.g., non-covalent bond) and at least one analyte-antibody interaction. Formation of the analyte-antibody complex can occur before, after or simultaneously with formation of the avidin-biotin interaction. The presence of the analyte-antibody complex is then determined using techniques such as, for example, light scattering and/or light absorbance. Other techniques involving, for example, fluorescence can be used.

Without wishing to be bound by theory, it is believed formation of the agglomeration according to the methods disclosed herein results in an increased sensitivity (e.g., with respect to time, presence and/or amount) in assaying the sample. In particular, it is believed that, by using the methods disclosed herein to form an agglomeration, the signal corresponding to a given concentration of analyte is increased relative to certain other assay techniques. It is believed that this can result in the ability to detect smaller amounts of analyte relative to certain other assay techniques, and/or the ability to detect a given amount of analyte faster relative to certain other assay techniques.

Figure 3:
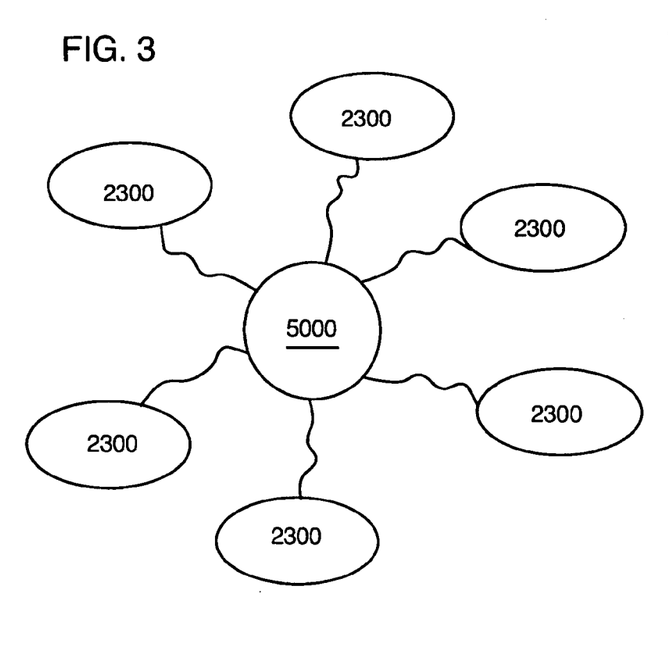
FIG. 3 is a schematic representation of an embodiment of a particle.
Figure 4:
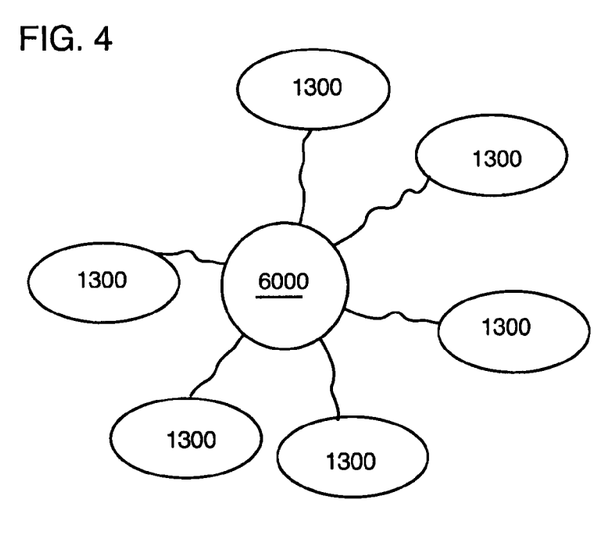
FIG. 4 is a schematic representation of an embodiment of a particle.

While the foregoing discussion has been with respect to particles having a single biotin or a single avidin molecule bonded thereto, the invention is not so limited. For example, as shown in FIG. 3, one or more particles 5000 can have a plurality of biotin molecules 2300 bonded thereto. As another example, as shown in FIG. 4, one or more particles 6000 can have a plurality of avidin molecules bonded thereto 1300. Without wishing to be bound by theory, it is believed that having multiple avidin molecules bonded to one or more particles and/or multiple biotin molecules bonded to one or more particles can increase the sensitivity of the assay by increasing the size of the agglomeration and/or the speed with which the agglomeration is formed.

Moreover, while the foregoing discussion has been with respect to a biotin molecule bonded to a particle, the invention is not so limited. For example, some or all of the biotin may initially in an unbound state (e.g., introduced into the sample without being bonded to a particle). Similarly, the avidin molecule need not be bound to a particle. For example, the avidin molecule can be bound to an antibody with neither the antibody nor the avidin bound to a particle. In some embodiments, the avidin is bound to both a particle and an antibody (e.g., the avidin is bound to the particle as described above, and the antibody is bound to the avidin rather than being directly bound to the particle).

Figure 5:
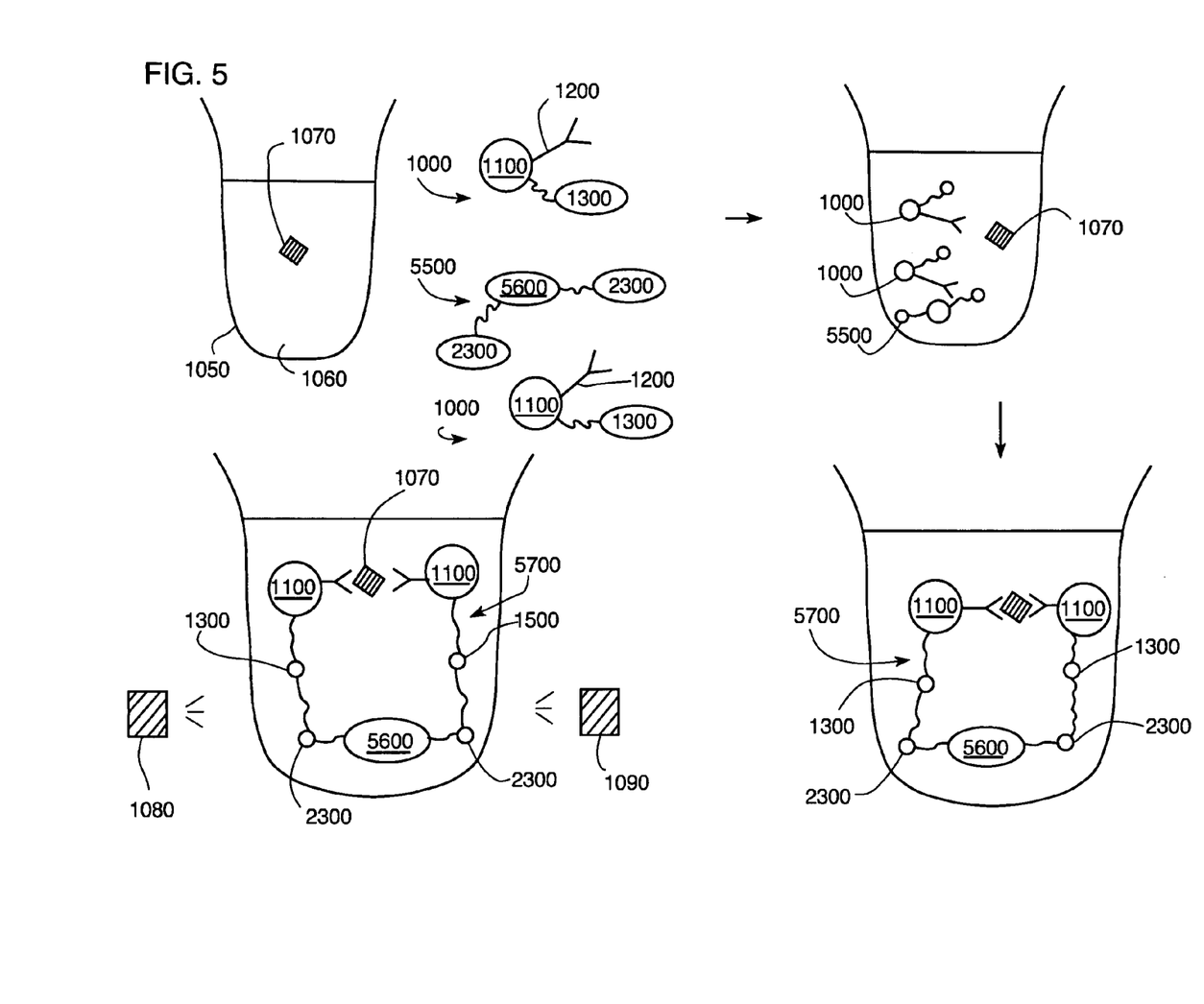
FIG. 5 is a schematic representation of an embodiment of a method.

Furthermore, while the foregoing discussion has been with respect to methods and agglomerations in which a particle has both an antibody and a biotin molecule bound thereto, the invention is not so limited. For example, FIG. 5 shows a schematic representation of a method of performing an assay using a plurality of first articles 1000 and a plurality of second articles 5500, with each article 5500 including a particle 5600 having two biotin molecules 2300 bound thereto and no antibodies bound thereto. In certain embodiments, the method of performing the assay involves forming an agglomeration 5700 including articles 1000 and 5500 via a combination of avidin-biotin interactions (e.g., non-covalent bond) and at least one analyte-antibody interaction. Formation of the analyte-antibody complex can occur before, after or simultaneously with formation of the avidin-biotin interaction. The presence of the analyte-antibody complex is then determined using techniques such as, for example, light scattering and/or light absorbance. Other techniques involving, for example, fluorescence can be used.

Although the foregoing discussion has been with respect to avidin and biotin, other binding pairs can also be used. More generally, for example, any ligand having at least two binding sites for another ligand (binding partner) can be used. Examples of ligands that can be used instead of avidin include other biotin-binding proteins, immunoglobulins, lectin, and metal chelating agents. Combinations of these ligands can be used. Likewise, any ligand that binds with avidin (or the avidin substitute) can be used instead of biotin. Examples of such ligands include protein A, protein G, haptens, saccharides and metal ions. Combinations of these ligands can be used.

In some embodiments, the ligands that form the binding pair (e.g., biotin-avidin) have an affinity constant of at least about $1 \times 10^4$ liters per mole (e.g., at least about $1 \times 10^5$ liters per mole, at least about $1 \times 10^6$ liters per mole). As used herein, the term "affinity constant" refers to the ratio of the association rate to the dissociation rate. For example, the affinity constant of the avidin-biotin binding is the ratio of the association rate of the avidin-biotin complex to the dissociation rate of the avidin-biotin complex. The affinity constant can be measured by methods known to those skilled in the art. For example, the affinity constant can be measured as follows. The ligands are mixed and a dialysis is performed that separates bound and free components into two compartments. When equilibrium is attained the concentrations are then determined using one or more standard techniques (e.g., by labeling one of the components).

In certain embodiments, the ligands that form the binding pair (e.g., biotin-avidin) have an affinity constant that is greater than the affinity constant of the antibody-analyte complex.

In embodiments, the antibodies used can be the same or different.

While the foregoing discussion has been with respect to antibodies, other ligands can be used. Such ligands include, for example, antigens, lectins, receptors, binding proteins, co-factors, vitamins, peptides, oligonucleotides, metal chelating agents, polysaccharides and derivatives thereof. Combinations of these ligands can be used.

Furthermore, the invention is not limited to antigens as the analyte. More generally, for example, the analyte can be selected from antibodies, vitamins, pesticides, drugs, steroids, peptides, oligonucleotides, oligosaccharides, hormones and toxins. Combinations of analytes can be assayed.

Examples of bodily fluids that can form the sample include serum, urine, blood, feces, sweat, saliva and/or tissue homogenates.

Examples of particles (e.g., solid phase particles) include metal particles, latex particles, silica particles, glass particles, paramagnetic particles, polymer particles, erythrocyte particles and liposome particles. In some embodiments, a latex particle is used. In certain embodiments, a colloidal metal particle (e.g., colloidal gold particle) is used. Combinations of particles can be used.

The method performed at a temperature of from about 4° C. to about 50° C. (e.g., from about 25° C. to about 50° C., from about 35° C. to about 38° C., about 37° C.).

The sample can contain one or more buffers. Examples of buffers include MOPS, MES, HEPES, HEPPS, TES, ADA, tricine, bis-tricine, glycine, glycyl-glycine, tris, phosphate, carbonate, phthalate, barbital, borate and combinations thereof.

The sample can contain one or more surfactants. Examples of surfactants include alkyl polyoxyethylenes (e.g. tweens, brijs), alkyl phenyl polyoxyethylenes (e.g. tritons, NP-40), surfynols, block copolymers of polyoxyethylene-polyoxypropylenes (e.g. pluronics, tetronics), alkyl glucosides, bile acid derivatives, sulfobetaines, zwittergents, sulfosuccinates, glucamides and combinations thereof.

The sample can contain one or more accelerators. Examples of accelerators include polyethylene glycol, polysaccharides, sugars, PVP, inorganic salts and combinations thereof.

The following examples are illustrative only and not intended to be limiting.

Example I

This example describes an assay of human C-reactive protein (hCRP) using NeutrAvidin®, goat anti-hCRP antibody coated particles and biotin coated particles.

140 nm diameter Carboxylate modified latex (CML) particles (Interfacial Dynamics Corp.) were activated using 1-ethyl-3-(3-dimethylaminopropyl)carbodiimide (Sigma Chemical Co.) and N-hydroxysuccinimide (Pierce Endogen Co.) in 50 millimolar MES buffer, pH 5.5 at room temperature for 15 minutes, and then washed by hollow fiber crossflow-filtration (A/G Technologies Corp.) with 5 volumes of 50 millimolar MES buffer, pH 5.5 at room temperature. Then Neutravidin was added to the activated CML particles. The pH was adjusted to pH 7.0 by addition of 200 millimolar HEPES buffer pH 8.2, and then reacted for 3 hours at room temperature. The particles were washed by hollow fiber crossflow-filtration (A/G Technologies Corp.) with five volumes of 50 millimolar MES buffer, pH 5.5. These particles were then activated with 1-ethyl-3-(3-dimethylaminopropyl) carbodiimide (Sigma Chemical Co.) and a polyclonal goat anti-hCRP antibody (Good Biotech Corp.) was added to the particles and reacted at 4° C. overnight and then washed by centrifugation at 13,000 G three times with 50 millimolar Tris, 150 millimolar sodium chloride, 0.05% w/v sodium azide, pH 7.5.

A second group of particles was made by reacting sulfo-N-hydroxysuccinimide LC biotin (Pierce-Endogen Co.) with 220 nm aliphatic amine derivatized latex particles (Interfacial Dynamics Corp.) in 50 millimolar sodium phosphate, 0.9% w/v sodium chloride, and 0.05% w/v sodium azide pH 7.5 at 4° C. overnight.

The particles were washed using a hollow fiber crossflow-filtration cartridge (A/G Technologies Corp.), with 5 volumes of 50 millimolar sodium phosphate, 0.9% w/v sodium chloride, 0.05% w/v sodium azide, pH 7.5 at room temperature.

Calibrator solutions of hCRP were made by addition of varying amounts of hCRP (Cortex Biochem) to aliquots of 5% w/v Bovine serum albumin in 50 millimolar sodium phosphate, 0.9% w/v sodium chloride, 0.05% w/v sodium azide, pH 7.5.

The assay was run on a Roche Cobas MIRA® automated clinical chemistry analyzer as follows. The analyzer was programmed to pipette 5 µL of calibrator solution of hCRP and 50 µL of the NeutrAvidin® and goat anti-hCRP coated particle solution followed by the addition of 50 µL of the biotin coated particle solution. Absorbance readings were then taken in an automated fashion every 25 sec for 500 sec at 600 nm at 37° C.

Figure 6:
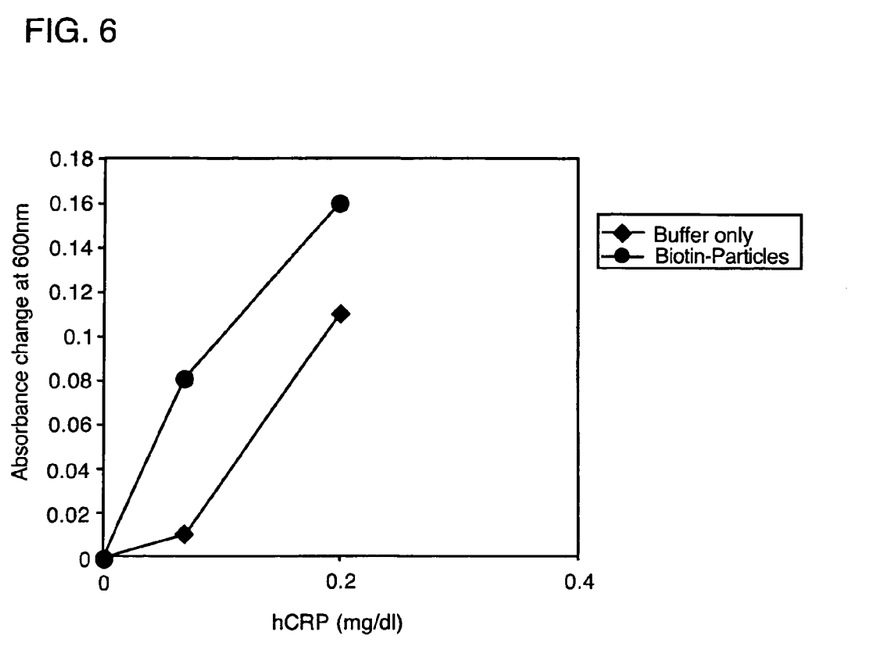
FIG. 6 is a plot showing human C-reactive protein (hCRP) concentration versus absorbance change at 600 nm with and without addition of the biotin derivatized particles.

The results are shown in FIG. 6.

Example II

This example describes an assay of hCRP using NeutrAvidin®, goat anti-hCRP antibody coated particles and biotin-dextran conjugates.

NeutrAvidin® and goat anti-hCRP antibody coated particles were made as described in Example I. Biotin-dextran conjugate was synthesized as follows. 2,000,000 MW dextran (Sigma Chemical Co.) was oxidized to polyaldehyde by reaction with sodium periodate overnight at 4° C. then dialyzed against three changes of water at 4° C. Biotin hydrazine (Pierce Chemical Co.) was then added in 60 mm Phosphate buffer pH 7.5 and reacted for 2 hours at room temperature. The conjugate was then purified by dialysis against three changes of 50 millimolar sodium phosphate, 0.9% w/v sodium chloride, 0.05% w/v sodium azide, pH 7.5 at 4° C. in 10,000 MW cut-off dialysis tubing (Pierce Endogen Co.).

Calibrator solutions of hCRP were made by addition of varying amounts of hCRP (Cortex Biochem, Inc.) to aliquots of 5% w/v Bovine serum albumin in 50 millimolar sodium phosphate, 0.9% w/v sodium chloride, 0.05% w/v sodium azide, pH 7.5.

The assay was run on a Roche Cobas MIRA® automated clinical chemistry analyzer as follows. The analyzer was programmed to pipette 5 µL of calibrator solution of hCRP and 50 µL of the NeutrAvidin® and goat anti-hCRP coated Particle solution followed by the addition of 50 µL of the biotin dextran conjugate solution. Absorbance readings were then taken in an automated fashion every 25 sec for 500 sec at 600 nm at 37° C.

Figure 7:
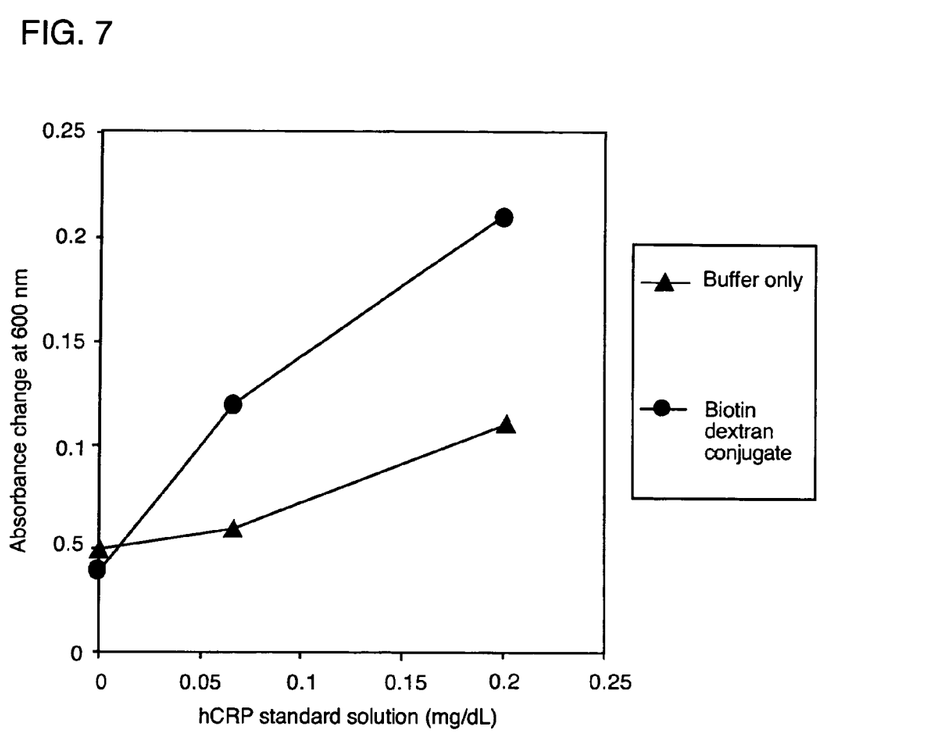
FIG. 7 is a plot showing a comparison of hCRP concentration versus absorbance change at 600 nm with and without addition of the biotin-dextran conjugate.

The results are shown in FIG. 7.

Example III

This example describes an assay of human ferritin (hFerritin) using NeutrAvidin®, monoclonal anti-ferritin antibody coated particles and biotin coated particles or biotin-dextran conjugates.

Two separate solutions of NeutrAvidin® and mouse monoclonal anti-hFerritin antibody coated particles were made as described in Example I, each solution having a different mouse monclonal anti-hFerritin antibody (OEM Concepts, Inc.) immobilized on the particles.

A third particle solution of biotin coated particles were made as described in Example I. The biotin-dextran conjugate was made as described in Example II The first and second NeutrAvidin® and mouse monoclonal anti-hFerritin antibody coated particles solutions were diluted together in a 1:1 ratio. This reagent was then used in immunoassays in which the mixture of the first and second NeutrAvidin® and mouse monoclonal anti-hFerritin antibody coated particles solutions were added first and the biotin coated particles second. In separate experiments the biotin-dextran conjugate solution was used instead of the biotin coated particle solution. Calibrator solutions of human ferritin were made by addition of varying amounts of human ferritin (Cortex Biochem) to aliquots of 5% w/v Bovine serum albumin in 50 millimolar sodium phosphate, 0.9% w/v sodium chloride, 0.05% w/v sodium azide, pH 7.5.

The assay was run on a Roche Cobas MIRA® automated clinical chemistry analyzer as follows. The analyzer was programmed to pipette 5 µL of calibrator solution of hFerritin and 50 µL of the mixture of Neutravidin and mouse monoclonal anti-hFerritin antibody coated particle solutions followed by the addition of 50 µL of the biotin-coated particles or in separate experiments the biotin-dextran conjugate solution. Absorbance readings were then taken in an automated fashion every 25 sec for 500 sec at 600 nm at 37° C.

Figure 8:
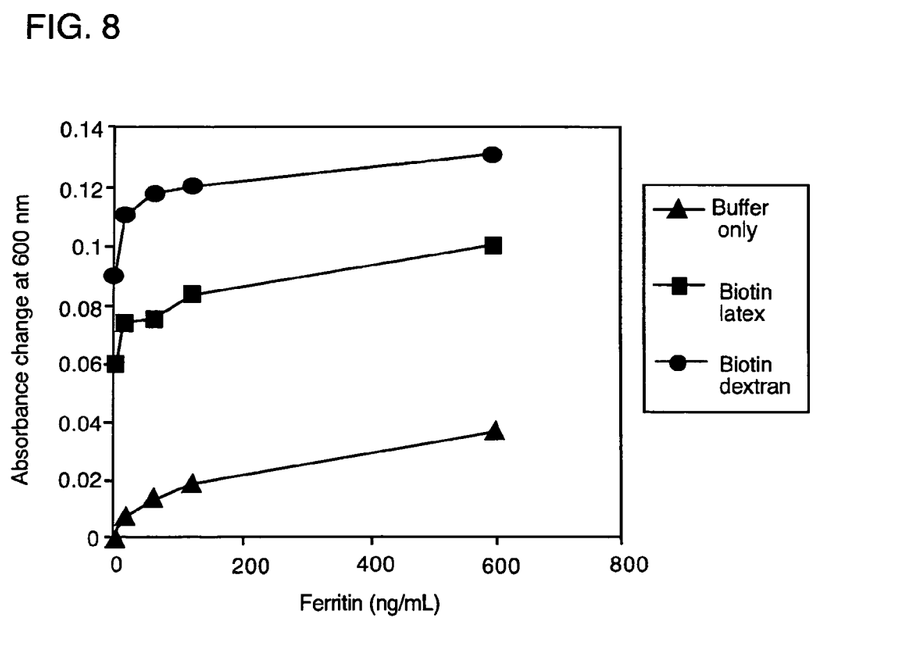
FIG. 8 is a plot showing a comparison of ferritin concentration versus absorbance change at 600 nm with and without addition of the biotin derivatized particles or biotin dextran conjugate.

The results are shown in FIG. 8.

Example IV

This example describes an assay of hCRP using NeutrAvidin®, goat anti-hCRP antibody coated gold colloid particles and biotin-dextran conjugates.

NeutrAvidin® (Pierce Chemical Co.) and polyclonal goat anti-hCRP antibody (Good Biotech Corp.) were passively adsorbed onto the 40 nm gold colloid in 10 mM Borate buffer at pH 8.6 by mixing for 30 minutes. The colloid surface was then blocked with 2% w/v bovine serum albumin and washed by three centrifugations at 2000 G for twenty-five minutes at room temperature.

Biotin-dextran conjugate was synthesized as described in example II.

The assay was run on a Roche Cobas MIRA™ automated clinical chemistry analyzer by programming the following method, 7.5 µL calibrator solution of hCRP was added to 75 µL of the gold colloid solution followed by the addition of 75 µL of the dextran-biotin conjugate solution. Absorbance readings were then taken in an automated fashion every 25 sec for 300 sec at 600 nm.

Figure 9:
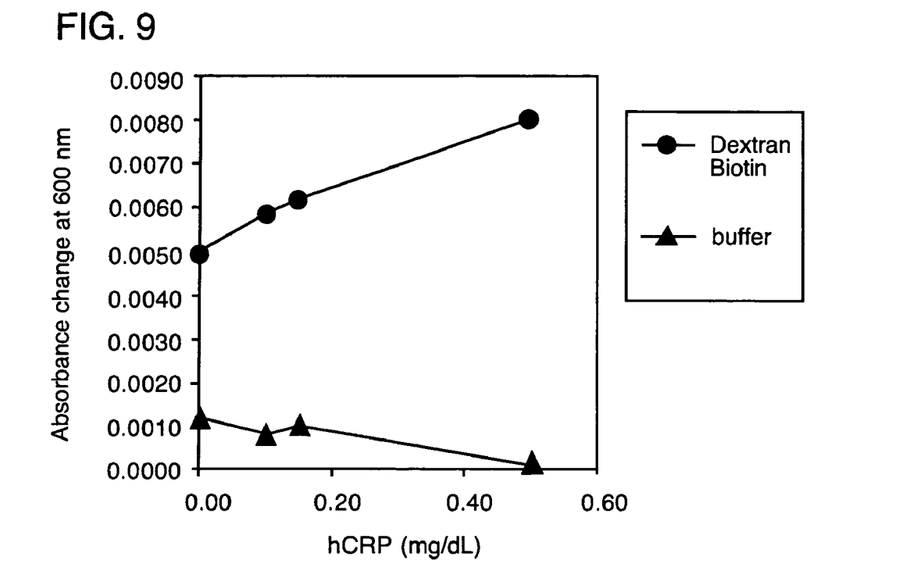
FIG. 9 is a plot showing a comparison of hCRP concentration versus absorbance change at 600 nm with and without addition of the biotin-dextran conjugate.

The results are shown in FIG. 9.

Example V

This example describes an assay of human luteinizing hormone (hLH) using NeutrAvidin® and polyclonal anti-hLH antibody coated particles, monoclonal anti-hLH coated particles and biotin-coated particles.

340 nm diameter Carboxylate modified latex (CML) particles (Interfacial Dynamics Corp.) were activated using 1-ethyl-3-(3-dimethylaminopropyl)carbodiimide (Sigma Chemical Co.) and N-hydroxysuccinimide (Pierce Endogen) and washed by hollow fiber crossflow-filtration (A/G Technologies Corp.) with two volumes of 50 millimolar MES buffer, pH 5.5 at room temperature. Then NeutrAvidin® was added to the activated CML particles. The pH was then adjusted to pH 7.0 by addition of 200 millimolar HEPES buffer pH 8.2 and reacted for 3 hours at room temperature. Separately polyclonal anti-hLH antibody (Cortex Biochem) was reacted with sulfo-N-hydroxysuccinimide LC biotin (Pierce-Endogen Co.) and then dialyzed to remove free biotin. The biotinylated antibody was then attached to the neutravidin coated latex particles through the binding of biotin to neutravidin on the particles.

A second particle solution was made by activating 340 nm Carboxylate modified latex particles (Interfacial Dynamics Corp.) using 1-ethyl-3-(3-dimethylaminopropyl) carbodiimide (Sigma Chemical Co.) and N-hydroxysuccinimide (Pierce Endogen) washing the particles by hollow fiber cross-flow-filtration (A/G Technologies Corp.) using two volumes of 50 millimolar MES buffer, pH 5.5 at room temperature. Then Bovine serum albumin (Sigma Chemical Co.) was added to the activated CML particles. The pH was then adjusted to pH 7.0 by addition of 200 millimolar HEPES buffer pH 8.2 and reacted for 3 hours at room temperature. The particles were then washed by hollow fiber crossflow-filtration (A/G Technologies Corp.) using 5 volumes of 50 millimolar sodium phosphate, 0.9% w/v sodium chloride, and 0.05% w/v sodium azide, pH 7.5 at room temperature. EDTA was added to the BSA particle suspension, to a final concentration of 10 millimolar. To this suspension of BSA particles was added m-maleimidobenzoyl-N-hydroxysuccinimide ester (Pierce Endogen) in DMSO. The reaction proceeded overnight at 4° C. The particles were then washed by hollow fiber cross-filtration (A/G Technologies Corp.) with five volumes of 50 millimolar MES buffer, pH 5.5. This was reacted with 1-ethyl-3-(3-dimethylaminopropyl)carbodiimide (Sigma Chemical Co.) and N-hydroxysuccinimide (Pierce Endogen) for 15 minutes at room temperature, then washed by hollow fiber crossflow-filtration (A/G Technologies Corp.) with two volumes of 50 millimolar MES buffer, pH 5.5 at room temperature. A mouse monoclonal anti-hLH antibody (OEM Concepts) was added and the pH was then adjusted to pH 7.0 by addition of 200 millimolar HEPES buffer pH 8.2 and reacted for 3 hours at room temperature. The particles were then washed by hollow fiber crossflow-filtration (A/G Technologies Corp.) using 5 volumes of 50 millimolar Tris buffer, 150 millimolar sodium chloride, 0.05% sodium azide, pH 7.5 at room temperature A biotin coated particle was made by the method described in Example I.

The NeutrAvidin® and polyclonal anti-hLH antibody coated particle solution and the mouse monoclonal anti-hLH antibody coated particle solution were diluted together in a 1:1 ratio. This reagent was then used in immunoassays in which the mixture of the NeutrAvidin® and polyclonal anti-hLH antibody coated particle solution and monoclonal anti-hLH coated particles were added first and the biotin coated particles second. Calibrator solutions of hLH were made by addition of varying amounts of human Luteinizing hormone (Cortex Biochem) to aliquots of 1% w/v Bovine serum albumin in 50 millimolar tris buffer, 150 millimolar solution of sodium chloride, and 0.05% sodium azide.

The assay was run on a Roche Cobas MIRA® automated clinical chemistry analyzer as follows. The analyzer was programmed to pipette 10 µL of calibrator solution of hLH and 75 µL polyclonal and Neutravidin® coated particle and monoclonal coated particle mixture followed by the addition of 75 µL of the biotin coated particles suspension. Absorbance readings were then taken in an automated fashion every 25 sec for 1250 sec at 340 nm.

Figure 10:
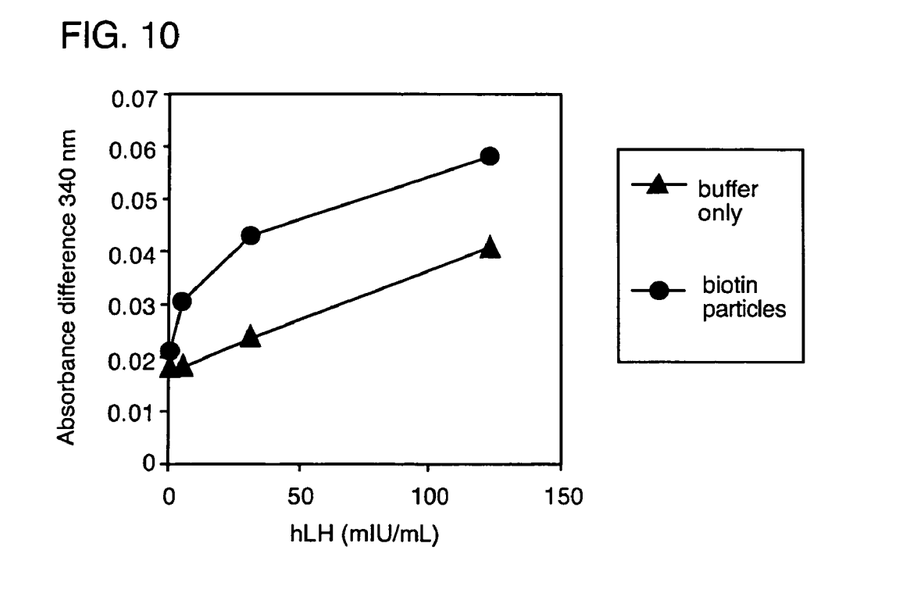
FIG. 10 is a plot showing a comparison of human luteinizing hormone (hLH) concentration versus absorbance change at 340 nm with and without addition of the biotin derivatized particles.

The results are shown in FIG. 10.

Example VI

This example describes an assay of hCRP using NeutrAvidin®, goat anti-hCRP dextran conjugates and biotin particles.

NeutrAvidin® (Pierce Endogen Co.) and goat anti-hCRP dextran conjugate was synthesized as follows. 2,000,000 MW dextran (Sigma Chemical Co.) was oxidized to polyaldehyde by reaction with sodium periodate overnight at 4° C. then dialyzed against three changes of water at 4° C. Neutravidin® (Pierce Endogen Co.), commercially available goat anti-hCRP (Good Biotech Corp.) and dextran polyaldehyde were then mixed in a 0.5:1:1 ratio by mass and reacted overnight at 4° C. The product was then dialyzed against three changes of 50 millimolar Tris buffer, 150 millimolar sodium chloride and 0.05% w/v sodium azide pH 7.5 in 300,000 MW cut-off cellulose acetate dialysis tubing (Spectrum Medical Industries, Inc.) at 4° C.

The biotin coated particle was made by the method described in Example I. The assay was run on a Roche Cobas MIRA® automated clinical chemistry analyzer as follows. The analyzer was programmed to pipette 5 µL of calibrator solution of hCRP and 50 µL of the mixture of Neutravidin and anti-hCRP antibody-dextran conjugate followed by the addition of 50 µL of the biotin-coated particles. Absorbance readings were then taken in an automated fashion every 25 sec for 500 sec at 600 nm at 37° C.

Figure 11:
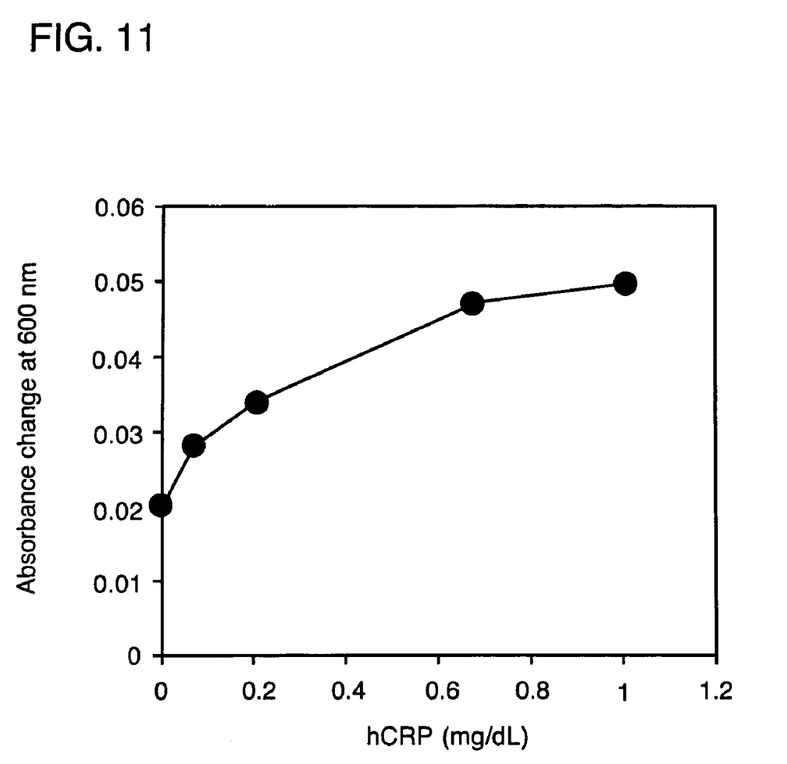
FIG. 11 is a plot showing a comparison of hCRP concentration versus absorbance change at 600 nm when assayed using NeutrAvidin® and goat anti-hCRP dextran conjugates and biotin particles.

The results are shown in FIG. 11.

Other embodiments are in the claims.

What is claimed is:

1. A set of articles for binding an analyte in a mixture to form a cross-linked assembly, formation of said assembly effecting a detectable increase in mixture turbidity compared to a mixture of said articles in the absence of said analyte, each article in said set of articles being unattached to any immobile solid surface, said set of articles comprising:
   a) a first analyte-binding substance that specifically binds said analyte, said first analyte-binding substance being attached to a first particle either directly or via a linker, said first particle also being attached to a first member of a specific binding pair;
   b) a second particle attached to a second member of said specific binding pair;
   c) a second analyte-binding substance that specifically binds said analyte, said second analyte-binding substance being attached to a third particle directly or via a linker;
   said first analyte-binding substance and said second analyte-binding substance being capable of binding a single analyte molecule simultaneously.

2. The set of articles of claim 1, wherein said first analyte-binding substance is a first antibody.

3. The set of articles of claim 1, wherein said second analyte-binding substance is a second antibody.

4. The set of articles of claim 1, wherein said first analyte-binding substance comprises a first oligonucleotide.

5. The set of articles of claim 1, wherein said second analyte-binding substance comprises a second oligonucleotide.

6. The set of articles of claim 1, wherein said specific binding pair is an avidin-biotin binding pair.

7. The set of articles of claim 1, wherein each of said first particle and second particle is independently selected from the group consisting of metal particles, latex particles, silica particles, glass particles, paramagnetic particles, polymer particles, erythrocyte particles and liposome particles.

8. A method of assay for an analyte comprising, providing the set of articles of claim 1 in the presence of a sample being assayed for said analyte, allowing said cross-linked assembly to form, and measuring the turbidity of a mixture comprising said cross-linked assembly, wherein the analyte is indicated by an increase in turbidity compared to the turbidity in the absence of said analyte.

* * * * *